United States Patent [19]

Kirk et al.

[11] Patent Number: 5,191,071

[45] Date of Patent: Mar. 2, 1993

[54] MONOESTERS OF GLYCOSIDES AND A PROCESS FOR ENZYMATIC PREPARATION THEREOF

[75] Inventors: Ole Kirk, Copenhagen N, Denmark; Frederik Björkling, Helsingborg, Sweden; Sven E. Godtfredsen, Vaerlose, Denmark

[73] Assignee: Novo Nordisk A/S, Denmark

[21] Appl. No.: 725,881

[22] Filed: Jun. 28, 1991

Related U.S. Application Data

[63] Continuation of Ser. No. 465,130, Feb. 20, 1990, abandoned.

[30] Foreign Application Priority Data

Aug. 21, 1987 [DK] Denmark ............... 4388/87

[51] Int. Cl.$^5$ ............... C07H 15/04; C07H 15/203; C12P 7/62
[52] U.S. Cl. ............... 536/4.1; 536/18.5; 536/18.6; 536/115; 536/119; 536/17.2; 536/17.5; 435/101; 435/198; 435/219; 435/252.1; 435/253.3; 435/874; 435/931; 252/174.17; 252/174.18
[58] Field of Search ............... 536/18.5, 18.6, 115, 536/119, 4.1, 17.2, 17.5; 435/101, 198, 219, 252.1, 253.3, 931, 874; 252/174.17, 174.18

[56] References Cited

U.S. PATENT DOCUMENTS

| | | | |
|---|---|---|---|
| 3,597,417 | 8/1971 | Myhre | 536/18.5 |
| 3,628,928 | 12/1971 | Gaydusch | 44/70 |
| 3,909,356 | 9/1975 | Suzuki et al. | 435/72 |
| 4,451,565 | 5/1984 | Gatfield et al. | 435/135 |
| 4,614,718 | 9/1986 | Seino et al. | 435/931 |
| 4,683,299 | 7/1987 | Kea et al. | 536/115 |
| 4,708,875 | 11/1987 | Godtfredsen et al. | 435/174 |
| 4,713,436 | 12/1987 | Downs et al. | 536/115 |
| 4,716,152 | 12/1987 | Kruger et al. | 536/4.1 |
| 4,826,962 | 5/1989 | Rathbone et al. | 435/100 |
| 4,859,589 | 8/1989 | Godtfredsen et al. | 435/100 |
| 4,952,687 | 8/1990 | Bodor et al. | 536/115 |
| 4,959,459 | 9/1990 | David et al. | 536/1.1 |
| 5,036,055 | 7/1991 | Ohnuma et al. | 536/17.1 |
| 5,041,424 | 8/1991 | Saulnier et al. | 536/17.1 |

FOREIGN PATENT DOCUMENTS

| | | |
|---|---|---|
| 2856716 | 7/1979 | Fed. Rep. of Germany . |
| 62-289190 | 12/1987 | Japan . |
| 63-112993 | 5/1988 | Japan . |

OTHER PUBLICATIONS

Sweers et al (J. Amer. Chem. Soc. 108, 1986, pp. 6421-6422).
Havlinova et al, Tenside Detergents, 1978, pp. 72-74.
Tulloch et al, Canadian Journal of Chemistry, vol. 46, 1968, pp. 2485-2493.
Reinefeld et al, Liebigs Ann. Chen, 747, 1971, pp. 39-44.
Lazar et al, Proceedings American Oil Chemists' Society, World Conference On Emergency Technologies In The Fats And Oil Industry, Ed. Baldwin, 1986, pp. 346-354.

*Primary Examiner*—Ronald W. Griffin
*Attorney, Agent, or Firm*—Rosenman & Colin

[57] ABSTRACT

Compounds of the formula (R-COO)$_n$X-OR$^1$, wherein R$^1$ is optionally substituted alkyl, phenyl, or alkyl phenyl, n is 1, 2 or 3, X is a carbohydrate moiety, and R is optionally substituted alkyl, have superior effects as additives in detergents. These compounds can be prepared by esterification of glycosides using specific enzymes.

38 Claims, 1 Drawing Sheet

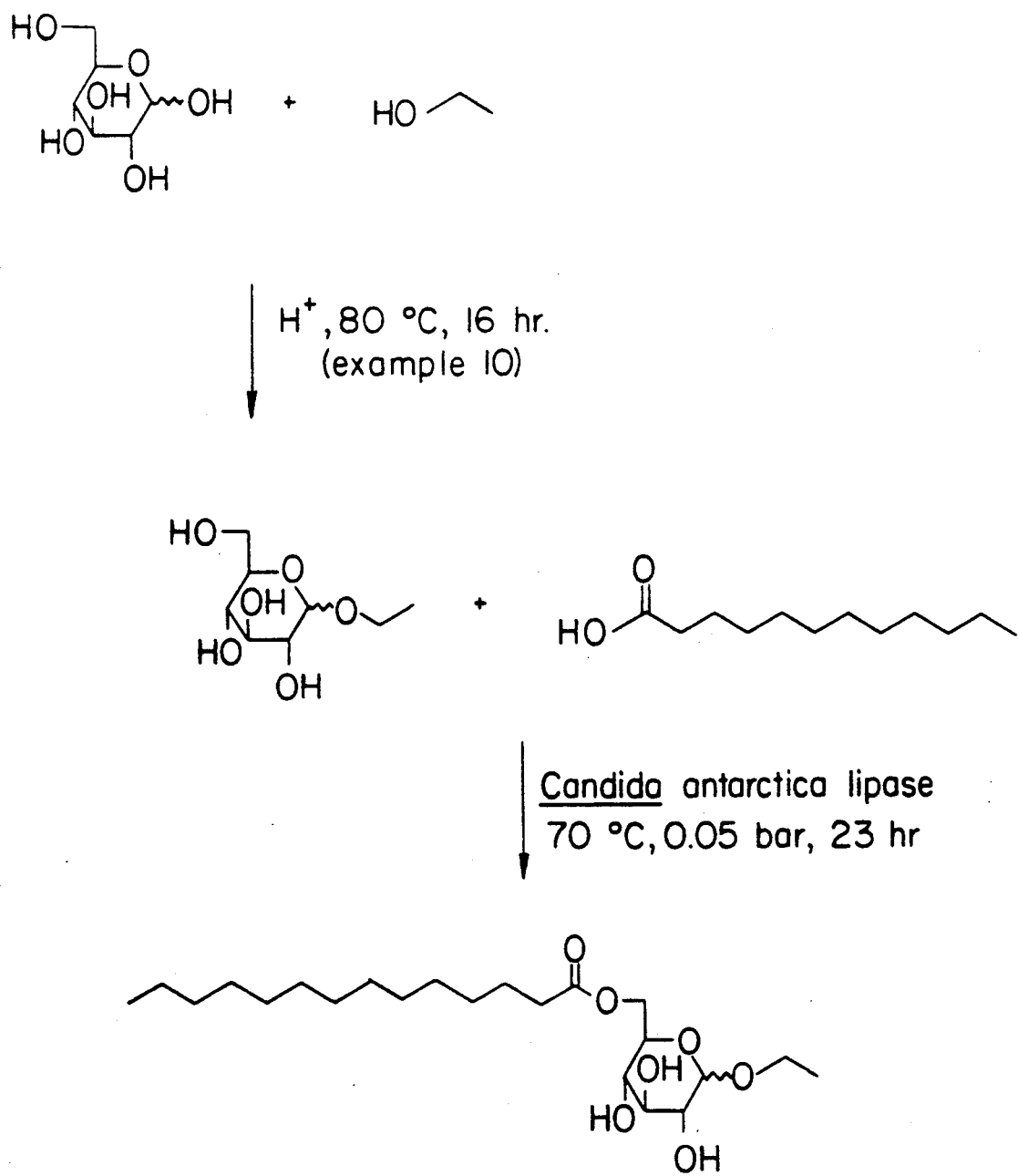
FIG. I

MONOESTERS OF GLYCOSIDES AND A PROCESS FOR ENZYMATIC PREPARATION THEREOF

This is a continuation application of co-pending application Ser. No. 07/465,130, filed Feb. 20, 1990, now abandoned.

SUMMARY OF THIS INVENTION

This invention relates to novel monoesters of glycosides and to a process for enzymatic syntheses of such compounds.

BACKGROUND OF THIS INVENTION

Surface active compounds constitute an exceedingly important class of industrial organic chemicals finding a wide variety of uses, e.g. as detergent for washing purposes, as emulsifiers in food and feed products, or even as functional ingredients in many personal care products as shampoos, moisturing creams etc.

Basically, surfactants are, on the molecular level, characterised by and owe their properties to presence of hydrophobic and hydrophilic regions within the individual surfactant molecules. This particular constellation can be established in numerous fashions, e.g. by combining sulphonic acid residue, a quarternised ammonium entity or a glycerol moiety with an alkyl chain as is the case in the linear alkyl surfactants, the quarternised alkyl amines, and the monoglycosides, respectively. In the actual design of such surfactant molecules major consideration is given to the detailed molecular architecture of the compounds, important issues being the precise balance between the hydrophilic and hydrophobic domains of the surfactant molecules, and the actual special arrangements of these parts of the molecules. Besides, consideration is obviously given to the possibilities of actually producing the surfactants in high yielding processes and on the basis of raw materials available at reasonable costs. The environmental issues related to the eventual loading of the surfactant into the environment are finally a matter of major concern.

Due to these considerations there have over the years been a keen interest in preparing surfactant molecules on the basis of sugars and fatty acids, e.g. as sugar esters. Such conjugates were expected to exhibit surface active properties due to the presence of the hydrophilic sugar regions and the hydrophobic fatty acid residues. The balance, and thus the precise properties of the conjugates, might be varied through changes of the nature of the sugar and the fatty acid residues; the materials would be producable from exceedingly cheap raw materials; and the surfactants, being composed of and degradable into natural constitutents, would not be harmful to the environment.

As a specific example of surfactants, reference is made to *Phillip.J.Coconut stud.* 5 (1980), 51 *et sec.*, wherein coconut fatty acid esters of methyl glucopyranoside is described. However, there is no mentioning in this paper about these surfactants being used as additives to detergents. As examples of specific commercially us®d surfactants which are additives to detergents, Berol 065 and Berol 160 (fatty alcohol ethoxylates) manufactured by Berol AB, Sweden, can be mentioned.

Synthesis and production of pure sugar esters by conventional means have, in spite of many attempts, turned out to be quite difficult. This is due, among other things, to the presence of several chemically similar groups in the sugar molecules which, accordingly, are esterified at several positions by exposure to esterification reagents. Sugar esters prepared by chemical means are, therefore, usually mixtures of compounds differing in respect to the degree of esterification and in the positions of the acyl groups on the carbohydrate moiety of the products. Since, in addition, the chemical procedures for chemical esterification turn out to be quite cost intensive, the sugar esters so far made available on an industrial scale find a rather limited use only.

In view of the difficulties encountered in production of sugar esters by chemical means and the attractiveness of these compounds as industrial surfactants, much attention has during the recent years been devoted to the possibility of utilising enzymes for synthesis of the sugar esters. One major rationale behind this interest is that enzymes are known to exhibit a high degree of regio- and enantioselectivity which might be exploited for selective esterification of one or more hydroxy groups in sugar molecules. Cheap starting materials might be utilised in enzymatic processes which might, therefore, lead to low priced sugar esters of a high quality. The enzymes envisioned as catalysts in processes of this kind are primarily lipases which catalyse hydrolysis of ester bonds and which do, therefore, in principle, also catalyse the reverse reaction, i.e. ester synthesis.

The attempts to develop efficient enzymatic syntheses of sugar esters have, however, so far, been unsuccessful. One major reason for this failure is the major polarity difference between the two substrates of the esterification reaction, the sugar and the fatty acid or a derivative thereof, and the necessity of avoiding water in the reaction medium in order to drive the enzymatic reaction in the directions of synthesis. Few good solvents for both sugars and fatty acids or their derivatives are thus available and these solvents will often inactivate enzymes.

These difficulties inherent in enzymatic synthesis of sugar esters are reflected in the cases reported as for example in U.S. patent specification No. 4,614,718 and in *J.Am.Chem.Soc.* 108 (1986), 5638–5640 and 6421–6422, and 109 (1987), 3977–3981. These publications teach application of lipases for esterification of sorbitol and sorbital with fatty acids, and transesterification from activated esters of free fatty acids onto long chain glycosides with lipases, respectively. The poor yields, the low selectivity of the reactions and the toxicity of solvents applied in the processes revealed exclude, however, any technical utility, of the processes described.

U.S. patent specification No. 4,614,718 does not relate to esters of glycosides but to sugar or sugar alcohol esters of higher fatty acids.

The PCT application having international publication No. WO 86/05186 does not relate to esters of glycosides but to a process wherein the starting material has only one free hydroxy group.

U.S. patent specification No. 2,759,922 relates to a process for preparing diesters, triesters and tetraesters of glycosides. Said patent does not describe the preparation of pure monoesters of glycosides. No enzymatic reactions are described in said patent.

German Offenlegungsschrift No. 2,360,368 relates to esters of polyglycosides having a degree of glycosidation of from 1.1 to 4. No enzymatic reactions are described in said Offenlegungsschrift.

One object of this invention is to provide novel compounds.

A further object of this invention is to provide surfactants having superior effects.

A still further object of this invention is to provide surfactants which have superior effects when used in detergents.

A further object of this invention is to provide cleaning agent compositions with better cleaning effects.

A still further object of this invention is to provide a process for preparing monoesters of glycosides.

A still further object of this invention is to provide monoesters of glycosides of monosaccharides.

BRIEF DESCRIPTION OF THE DRAWING

The drawing shows Scheme 1, depicting the reactions producing ethyl glucoside and the esterification thereof.

DETAILED PRACTISE OF THIS INVENTION

It has now, surprisingly, been found that compounds of the general formula I $$R—COO—X—OR^1 \quad (I)$$

wherein $R^1$ represents alkyl with 2–6 carbon atoms or $R^1$ represents one of the groups

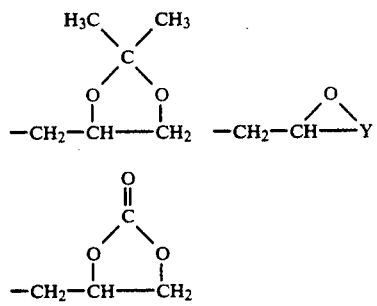

wherein Y represents methylene or ethylene, X represents a monosaccharide moiety carrying at the anomeric carbon atom H the group —$OR^1$ and carrying a RCOO— group at a primary hydroxy group, and R represents alkyl with 4–24 carbon atoms, have superior effects as surfactant.

In all monosaccharides—apart from ketoses, e.g. fructose—in formula I, the group designated —$OR^1$ is connected to the terminal carbon atom.

The parent monosaccharide as well as the compounds of formula I may be the α- or β-form.

The alkyl groups may be linear or branched The term "lower" indicates, when used in connection with alkyl groups and similar groups, that the alkyl group in question contains not more than 8 carbon atoms, preferably not more than 4 carbon atoms Preferably $R^1$ is an alkyl group. Preferably, the group $R^1$ contains 2, 3 or 4 carbon atoms. Examples of specific, preferred groups $R^1$ are ethyl, propyl, isopropyl and butyl, most preferred ethyl and isopropyl.

The process described below is expected to be the only process known by which it is possible to prepare acceptable yields of monoesters. Hence, monoesters of formula I have not previously been available X is a monosaccharide moiety consisting of one hexose or pentose unit. Preferred monosaccharides corresponding to the moiety X are glucose, fructose, ribose, mannose and galactose, the most preferred monosaccharides being glucose and galactose.

Preferred fatty acids corresponding to the moiety R—COO— in formula I are saturated and unsaturated fatty acids, preferably containing 6–22 carbon atoms. Examples of such fatty acids are hexanoic acid, heptanoic acid, octanoic acid, nonanoic acid, decanoic acid, dodecanoic acid, tetradecanoic acid, hexadecanoic acid, octadecanoic acid, eicosanoic acid, docosanoic acid, cis-9-octadecanoic 5 acid, cis,cis-9,12-octadecanoic acid and cis,cis,cis9,12,15-octadecatrienoic acid.

Examples of specific, preferred compounds of formula I are as follows: Ethyl 6-O-hexanoylglucoside, ethyl 6-O-heptanoylglucoside, ethyl 6-O-octanoylglucoside, ethyl 6-O-nonanoylglucoside, ethyl 6-O-decanoylglucoside, ethyl 6-O-dodecanoylglucoside, ethyl 6-O-tetradecanoylglucoside, ethyl 6-O-hexadecanoylglucoside, ethyl 6-O-octadecanoylglucoside, ethyl 6-O-eicosanoylglucoside, ethyl 6-O-docosanoylglucoside, ethyl 6-O-cis-9-octadecenoylglucoside, ethyl 6-O-cis,cis-9, 12-octadecadienoylglucoside, ethyl 6-O-cis,cis,cis-9,12,15-octadecatrienoylglucoside, isopropyl 6-O-hexanoylglucoside, isopropyl 6-O-heptanoylglucoside, isopropyl 6-O-octanoylglucoside, isopropyl 6-O-nonanoylglucoside, isopropyl 6-O-decanoylglucoside, isopropyl 6-O-dodecanoylglucoside, isopropyl 6-O-tetradecanoylglucoside, isopropyl 6-O-hexadecanoylglucoside, isopropyl 6-O-octadecanoylglucoside, isopropyl 6-O-eicosanoylglucoside, isopropyl 6-O-docosanoylglucoside, isopropyl 6-O-cis-9-octadecenoylglucoside, isopropyl 6-O-cis,cis-9,12-octadecadienoylglucoside, isopropyl 6-O-cis,cis,cis-9,12,15-octadecatrienoylglucoside, propyl 6-O-hexanoylglucoside, propyl 6-O-heptanoylglucoside, propyl 6-O-octanoylglucoside, propyl 6-O-nonanoylglucoside, propyl 6-O-decanoylglucoside, propyl 6-O-dodecanoylglucoside, propyl 6-O-tetradecanoylglucoside, propyl 6-O-hexadecanoylglucoside, propyl 6-O-octadecanoylglucoside, propyl 6-O-eicosanoylglucoside, propyl 6-O-docosanoylglucoside, propyl 6-O-cis-9-octadecenoylglucoside, propyl 6-O-cis,cis-9,12-octadecadienoylglucoside, propyl 6-O-cis,cis,cis-9,12,15-octadecatrienoylglucoside, butyl 6-O-hexanoylglucoside, butyl 6-O-heptanoylglucoside, butyl 6-O-octanoylglucoside, butyl 6-O-nonanoylglucoside, butyl 6-O-decanoylglucoside, butyl 6-O-dodecanoylglucoside, butyl 6-O-tetradecanoylglucoside, butyl 6-O-hexadecanoylglucoside, butyl 6-O-octadecanoylglucoside, butyl 6-O-eicosanoylglucoside, butyl 6-O-docosanoylglucoside, butyl 6-O-cis-9-octadecenoylglucoside, butyl 6-O-cis,cis-9,12-octadecadienoylglucoside and butyl 6-O-cis,cis-9,12,15-octadecatrienoylglucoside.

The compounds of formula I have surprisingly good effects as surfactants which, for example, can be illustrated by their cleaning effects, especially towards fatty and protein soiling.

The cleaning agents containing a compound of formula I may be in any convenient form, such as powders or liquids.

Typical examples of cleaning agents are laundry detergents, dishwash detergent and hard-surface cleaner. More specific examples are liquid heavy-duty detergents (with or without builders) and powder heavy-duty detergents (with or without phosphate builders)

The surfactant in the cleaning agents may be mainly of the non-ionic type (e.g. above 80%), or may be a combination of non-ionic (e.g. 20–80%) and another type of surfactant (e.g. 20–80% of anionic, cationic and/or zwitterionic). Examples of anionics are linear alkyl benzene sulphonates (LAS), fatty alcohol sulphates, fatty alcohol ether sulphates (AES), alpha-olefin sulphonates (AOS) and soaps.

Liquid and powder detergents may be formulated in analogy with "Frame formulations for liquid/powder heavy-duty detergents" (J. Falbe: Surfactants in Consumer Products. Theory, Technology and Application, Springer-Verlag 1987) by replacing all or part (e.g. 50%) of the non-ionic surfactant with a compound of formula I. Thus, liquid heavy-duty detergents may in addition to the compound of formula I comprise anionic surfactants, non-ionic surfactants, suds controlling agents, foaming boosters, enzymes, builders, formulation aids, optical brighteners, stabilizers, fabric softeners, fragrances, dyestuffs and water. Similarly, powder heavy-duty detergents may comprise anionic surfactants, non-ionic surfactants, suds controlling agents, foaming boosters, chelating agents, ion exchangers, alkalis, cobuilders, bleaching agents, bleach activators, bleach stabilizers, fabric softeners, antiredeposition agents, enzymes, optical brighteners, anticorrosion agents, fragrances, dyestuffs and blueing agents, formulation aids, fillers and water.

The superior effects of compounds of formula I are illustrated by example 34 below.

In addition, it has surprisingly been found that it is possible to prepare compounds of formula I

R—COO—X—OR$^1$  (I)

wherein R$^1$ represents alkyl with 2–6 carbon atoms or R$^1$ represents one of the groups

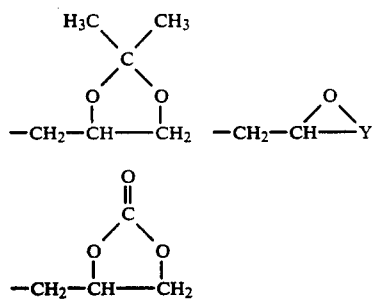

wherein Y represents methylene or ethylene, X represents a monosaccharide moiety carrying at the anomeric carbon atom the group —OR$^1$ and carrying a RCOO— group at a primary hydroxy group, and R represents alkyl with 4–24 carbon atoms, by condensing an acid or an ester of the general formula II

R—COOR$^2$  (II)

wherein R is as stated above, and R$^2$ represents hydrogen or lower alkyl, with a glycoside of the general formula III

HO—X—OR$^1$  (III)

wherein X and R$^1$ each is as defined above, in the presence of a catalyst, which process is characterized by said catalyst being a hydrolase. Briefly, compounds of formula I are prepared by enzymatic syntheses in very high yields using as substrates for the enzymatic esterification a monosaccharide carrying an alkyl group with 2–6 carbon atoms at the hydroxy group at the anomeric carbon atom and a free fatty acid or an ester thereof as the other substrate for the reaction. The products of the reaction are sugar esters carrying an alkyl group at the hydroxy group at the anomeric carbon atom. It is highly surprising, and it could not have been predicted, that a minor change of the sugar molecules at their anomeric carbons improves their behaviour as substrates dramatically and gives high yields and even regiospecific enzymatic esterifications.

Using this process it is possible to prepare a preparation containing more than 80%, preferably more than 90%, even more preferred more than 95%, of a compound of formula I. Such a preparation has superior, surprising properties as surfactant.

The enzymes which can be applied by the process of this invention are hydrolases, such as esterases, and lipases. The enzymes applied by the process of this invention may be used in a soluble state or the enzymes may be immobilised, if desired. Also, the enzymes may be modified by chemical or genetic methods in order to optimise their reactivity in regard to a specific reaction of interest.

Examples of specific enzymes which may be used by the process of this invention are porcine pancreatic lipase and microbial lipases obtained, e.g. from strains of Aspergillus, Rhizopus, Pseudomonas, Enterobacterium, Chromobacterium, Geotricium, Penicillium, Mucor, Candida, and Humicula. Examples of preferred strains are *Mucor Miehei, Candida antarctica, Pseudomonas cepacia* and *Humicola lanuginosa.*

Candida antartica was deposited at Deutsche Sammlung von Mikroorganismen (DSM) according to the Budapest Treaty under the deposit Nos. DSM 3855, DSM 3908 and DSM 3909 at the Sep. 29, 1986, Dec. 8, 1986 and Dec. 8, 1986, respectively.

Pseudomonas cephacia was deposited at DSM under No. 3959 on Jan. 30, 1987 and Humicola lanuginosa was deposited at DSM under the Nos. 3819 and 4109 on Aug. 13, 1986 and May 4, 1987, respectively.

Further lipases are obtainable from *Humicola brevispora, brevis var. thermoidea* and *insolens* which were deposited at DSM under the Nos. 4110, 4111 and 1800, respectively, on May 4, 1987, May 4, 1987 and Oct. 1, 1981, respectively.

Additional lipases are obtainable from the following strains, which are freely available to the public from Centralbureau voor Schimmelculturen (CBS), American Type Culture Collection (ATCC), Agricultural Research Culture Collection (NRRL) and Institute of Fermentation, Osaka (IFO) under the indicated deposit numbers: *Candida antarctica:* CBS 5955, ATCC 34888, NRRL Y-8295, CBS 6678, ATCC 28323, CBS 6821 and NRRL Y-7954; *Candida tsukubaensis:* CBS 6389, ATCC 24555 and NRRL Y-7792; *Candida auriculariae:* CBS 6379, ATCC 24121 and IFO 1580; *Candida humicola:* CBS 571, ATCC 14438, IFO 0760, CBS 2041, ATCC 9949, NRRL Y-1266, IFO 0753 and IFO 1527 and *Candida foliorum:* CBS 5234 and ATCC 18820.

The process of this invention may be carried out simply by mixing the glycoside of formula III with an acid or an ester thereof of formula II in the presence of the enzyme and, optionally, the reaction may be carried out in a solvent in which the enzyme exhibits the desired activity. Preferably, no solvent is added. If an organic solvent is used, it should have no deleterious effect on the enzyme. Examples of such solvents are ketones, hydrocarbons and ethers. Preferred solvents are pentane, hexane, heptane and 2-butanone.

Preferably, the reaction medium is non-aqueous or contains only the approximate amount of water which is needed to ensure a good reactivity and life-time of the applied enzyme.

Conveniently, the reaction temperature is in the range of about 20°-100° C., preferably about 30°-80° C. Preferably, the reaction is performed at a low pressure, preferably below about 0.05 bar.

This invention is illustrated by the following examples which, however, are not to be considered as limiting in any way the scope of protection.

GENERAL PROCEDURES $^1$H and $^{13}$C NMR-spectra were recorded on a Bruker WM 400 and a Bruker AM 500 spectrometer with TMS as internal reference. Optical rotation was measured on a Perkin-Elmer 241 polariometer, using 1 dm cuvette. Melting points are uncorrected. HPLC-analysis was performed on a Shimadzu LC-4A instrument (refractive index detector) using a Merck LiChrosorb ™ NH$_2$-column and 96% ethanol as eluent. Critical micelle concentrations were measured on a Kruss Tensiometer K10. Molecular distillation was performed on a KDL 1 unit from Leybold-Heraeus Isopropyl α-D-glucopyranoside n-propyl β-D-glucopyranoside and phenyl α-D-glucopyranoside were obtained as a gift from The Technical University of Denmark, Department of Organic Chemistry. Preparative liquid chromatography was performed on SiO$_2$ with a gradient of hexane-ethylacetate and methanol as eluent.

EXAMPLE 1

Preparation of ethyl 6-O-dodecanoyl-D-glucopyranoside

To a mixture of crude ethyl D-glucopyranoside (578 g, 2.78 mol, prepared according to example 10) and dodecanoic acid (751 g, 3.75 mol) in a stirred batch reactor at 70° C. was added immobilized lipase derived from *Candida antarctica* (29 g, prepared as described in Danish patent application No. 3250/88). Stirring was continued under reduced pressure (0.05 bar) and the progress of the ester synthesis was monitored by HPLC. After 23 hours the enzyme was removed by filtration (at 70° C.). Excess fatty acid was removed by repeated molecular distillation (105° C., 0.04 mbar) yielding 96% (1050 g) of crude product along with 2% ethyl D-glucoside and 2% of a mixture of diesters (HPLC analysis). The crude product was purified by chromatography Identification by $^1$H NMR-analysis showed a 1:1 mixture of α and β anomers (tables 42/46).

This reaction is illustrated in Scheme 1.

EXAMPLE 2

Preparation of ethyl 6-O-decanoyl-D-glucopyranoside

The title compound was obtained as a crude product (1030 g, 93% monoester, 5% ethyl D-glucopyranoside, 2% diesters) according to example 1 using ethyl D-glucopyranoside (625 g, 3.0 mol), decanoic acid (646 g, 3.75 mol) and immobilized lipase (31.5 g). The reaction was complete in 48 hours. NMR-spectra of the chromatographically purified product are given in tables 42/46.

EXAMPLE 3

Preparation of ethyl 6-O-tetradecanoyl-D-glucopyranoside

The title compound was obtained as a crude product (1160 g, 93% monoester, 4% ethyl D-glucopyranoside, 3% diesters) according to example 1 using ethyl D-glucopyranoside (609 g, 2.9 mol), tetradecanoic acid (834 g, 3.7 mol) and immobilized lipase (30.5 g). The reaction was complete in 46 hours. NMR-spectra of the chromatographically purified product are in accordance with the $^1$H and $^{13}$C NMR-spectra given for the pure α and β anomers in tables 4 a/4 b.

EXAMPLE 4

Preparation of ethyl 6-O-hexadecanoyl-D-glucopyranoside

The title compound was obtained as a crude product (1220 g, 91% monoester, 7% ethyl D-glucopyranoside, 2% diesters) according to example 1 using ethyl D-glucopyranoside (603 g, 2.9 mol), hexadecanoic acid (1001 g, 3.91 mol) and immobilized lipase (30.5 g). The reaction was complete in 48 hours. NMR-spectra of the chromatographically purified product are in accordance with the $^1$H and $^{13}$C NMR-spectra given for the pure α and β anomers in tables 4 a/4 b.

EXAMPLE 5

Preparation of ethyl 6-O-(cis-9-octadecenoyl)-D-glucopyranoside

The title compound was obtained as a crude product (1305 g, 90% monoester, 5% ethyl D-glucopyranoside, 5% diesters) according to example 1 using ethyl D-glucopyranoside (606 g, 2.9 mol), cis-9-octadecenoic acid (1111 g, 3.9 mol) and immobilized lipase (30.5 g). The reaction was complete in 48 hours.

EXAMPLE 6

Preparation of ethyl 6-O-octadecanoyl-D-glucopyranoside

The title compound was obtained as a crude product (1310 g, 90% mon©ester, 5% ethyl D-glucopyranoside, 5% diesters) according to example using a reaction temperature of 80° C., ethyl D-glucopyranoside (603 g, 2.9 mol), octadecanoic acid (1112 g, 3.9 mol) and immobilized lipase (30 g). The reaction was complete in 48 hours. NMR-spectra of the chromatographically purified product are in accordance with the $^1$H and $^{13}$C NMR-spectra given for the pure α and β anomers in tables 4 a/4 b.

EXAMPLE 7

Preparation of coconut oil fatty acid 6-O esterified ethyl D-glucopyranoside

Ethyl D-glucopyranoside (600 g, 2.9 mol) was esterified with a mixture of coconut oil fatty acids (containing 1% decanoic acid, 51% dodecanoic acid, 24% tetradecanoic acid, 13% hexadecanoic acid, 4% octadecanoic acid, 5% cis-9-octadecenoic acid and 2% cis,cis-9,12-octadecadienoic acid in a total amount of 3.0 mol) by the procedure described in example 1 using 30 g of immobilized lipase as catalyst. After 72 hours the reaction was complete yielding 1200 g of product (91% monoesters, 6% diesters and 3% ethyl D-glucopyranoside).

EXAMPLE 8

Preparation of ethyl 6-O-octanoyl-D-glucopyranoside

To a suspension of ethyl D-glucopyranoside (500 g, 2.4 mol prepared according to example 10) and octanoic acid (520 g, 3.6 mol) in hexane (1000 ml) in a stirred batch reactor at 70° C. (reflux) was added immobilized lipase (5 g Lipozyme TM, commercial available NOVO lipase prepared from a *Mucor Miehei*). Stirring was continued and the produced water was removed by azeotropic distillation. The progress of the reaction was followed by HPLC. As the product was being formed, the suspension gradually became a homogeneous solution (after 12 hours). After 52 hours the enzyme was removed by filtration and the solvent removed in vacuo. Excess fatty acid was removed by repeated molecular distillation giving a crude product (790 g, 91% monoester, 8% diester and 1% ethyl D-glucopyranoside). $H^1$ and $^{13}C$ NMR-spectra of the purified product were in accordance with the spectra for the pure α- and β-anomers given in tables 4 a/4 b.

EXAMPLE 9

Preparation of isopropyl 6-O-dodecanoyl-D-glucopyranoside

The title compound was prepared according to example 1 using isopropyl D-glucopyranoside (446 g, 2.01 mol prepared according to example 11). After 24 hours the reaction was complete and a crude product isolated (561.1 g, 73.4% monoester and 9.2% diester).

EXAMPLE 10

Preparation of ethyl D-glucopyranoside

Glucose (500 g, 2.78 mol) and a strong acid cation exchange resin (100 g Amberlyst TM 15, BDH Chemicals) was suspended in ethanol (2000 ml, 34.3 mol) The mixture was stirred at 80° C. for 16 hours. The progress of the reaction was followed by HPLC. The ion exchange resin was removed by filtration and the solution was treated with activated carbon (10 g). After filtration the ethanol was removed in vacuo giving ethyl D-glucopyranoside (a 1:1 mixture of α and β anomers) as a syrup (578 g, quantitative yield).

EXAMPLE 11

Preparation of isopropyl D-glucopyranoside

The title compound was prepared in quantitative yield by the procedure described in example 10 using isopropanol (2000 ml, 26 mol) and glucose (500 g, 2.78 mol).

EXAMPLE 12-17

Preparation of 6-O-esters of pure ethyl β-D-glucopyranoside

General procedure:

Ethyl β-D-glucopyranoside (3.0 g, 14 mmol prepared according to example 24) was dissolved/suspended in melted fatty acid (typical 28 mmol) at 70° C. Immobilized lipase (typical 0.5 g Lipozyme TM, see example 8) was added and the mixture was stirred at reduced pressure (0.05 bar). The progress of the reaction was followed by HPLC. The reaction of this mixture was diluted with acetone and the enzyme was removed by filtration. The solvent was removed in vacuo and the product was recovered by chromatography on $SiO_2$. For $^1H$ and $^{13}C$ NMR (see table 4 a) it was further characterised by melting points (m.p.), optical rotation ($[α]D$) and critical micelle concentration (CMC) measurement (given in table 3).

The experimental details from the different examples are shown in table 1.

TABLE 1

| Example | Fatty acid | g | mmol | Lipozyme g | Reaction time hours | Yield % |
|---|---|---|---|---|---|---|
| 12 | Octanoic | 8.3 | 58 | 1.0 | 240 | 75 |
| 13 | Decanoic | 5.0 | 28 | 0.5 | 64 | 81 |
| 14 | Dodecanoic | 5.7 | 28 | 0.5 | 24 | 87 |
| 15 | Tetradecanoic | 6.6 | 28 | 0.5 | 22 | 83 |
| 16 | Hexadecanoic | 7.3 | 28 | 0.5 | 40 | 77 |
| 17 | Octadecanoic | 8.2 | 28 | 0.5 | 76 | 76 |

Experimental details form the preparation of 6-O-esters of pure β-D-glucopyranoside.

EXAMPLE 18-23

Preparation of 6-O-esters of pure ethyl α-D-glucopyranoside

General procedure

Ethyl α-D-glucopyranoside (2.0 g, 9 mmol prepared according to example 25) was dissolved/suspended in melted fatty acid (typical 18 mmol). Immobilized lipase (typical 0.33 g) was added as in example 12-17. $^1H$ and $^{13}C$ NMR (see table 4 b). Melting points (m.p.), optical rotation ($[α]D$) and critical micelle concentration (CMC) measurement (these data are presented in table 3).

The experimental details from the different examples are shown in table 2.

TABLE 2

| Example | Fatty acid | g | mmol | Lipozyme g | Reaction time hours | Yield % |
|---|---|---|---|---|---|---|
| 18 | Octanoic | 9.3 | 54 | 0.67 | 312 | 50 |
| 19 | Decanoic | 5.0 | 27 | 0.33 | 192 | 71 |
| 20 | Dodecanoic | 3.8 | 18 | 0.33 | 76 | 71 |
| 21 | Tetradecanoic | 4.4 | 18 | 0.33 | 36 | 76 |
| 22 | Hexadecanoic | 4.9 | 18 | 0.33 | 72 | 74 |
| 23 | Octadecanoic | 5.5 | 18 | 0.33 | 52 | 83 |

Experimental details form the preparation of 6-O-esters of pure α-D-glucopyranoside.

TABLE 3

Physical data of the products from example 12-23:

| Example | Anomer α or β | Fatty acid | m.p. °C. | $[α]_D^{25}$ | CMC* |
|---|---|---|---|---|---|
| 12 | β | Octanoic | 79-80 | −52.4 (c = 1.0) | >500 |
| 18 | α | Octanoic | syrup | 70.9 (c = 1.1) | >500 |
| 13 | β | Decanoic | 82-83 | −49.7 (c = 1.0) | 110 |
| 19 | α | Decanoic | syrup | 63.0 (c = 1.3) | 69 |
| 14 | β | Dodecanoic | 77-78 | −46.7 (c = 1.1) | 6.9 |
| 20 | α | Dodecanoic | syrup | 60.7 (c = 1.4) | 4.7 |
| 15 | β | Tetradecanoic | 82-83 | −43.5 (c = 1.2) | 24 |
| 21 | α | Tetradecanoic | 42-45 | 54.5 (c = 1.3) | 2.9 |
| 16 | β | Hexadecanoic | 90 | −42.4 (c = 1.0) | 4.0 |
| 22 | α | Hexadecanoic | 46-51 | 49.9 | 3.9 |

TABLE 3-continued

| | | Physical data of the products from example 12-23: | | | |
|---|---|---|---|---|---|
| Example | Anomer α or β | Fatty acid | m.p. °C. | $[\alpha]_D^{25}$ | CMC* |
| 17 | β | Octadecanoic | 93-94 | (c = 1.1) −39.7 | 2.6 |
| 23 | α | Octadecanoic | 54-56 | (c = 1.0) 48.4 (c = 1.1) | ** |

*$10^{-5}$ mol/l, all measured in $CHCl_3$.
**The product was too insoluble.

EXAMPLE 24

Preparation of ethyl β-D-glucopyranoside

To a suspension of silver carbonate (30 g, 0.11 mol) was added 2,3,4,6-tetra-O-acetyl-β-D-glucopyranosyl bromide (41.1 g, 0.1 mol) in small portions over a period of 40 min. The mixture was stirred overnight, then diluted with dichloromethane (40 ml) and filtrated through celite and activated carbon. Ethyl 2,3,4,5-tetra-O-acetyl-β-D-glucopyranoside (23.4 g, 62%) crystallized upon concentration.

The ethyl 2,3,4,6-tetra-O-acetyl-glucopyranoside was deacetylated with 1M sodium methoxide (2 ml) in Methanol (80 ml) for 20 hours at room temperature. The mixture was neutralized with Amberlite TM IR-120 (H+-form) and concentrated in vacuo to give the product in quantitative yield as a hygroscopic solid.

EXAMPLE 25

Preparation of ethyl α-D-glucopyranoside

Ethyl D-glucopyranoside (30 g, prepared as described in example 10) with an anomeric ratio α:β=1:1 was dissolved in 0.05M acetate buffer (400 ml, pH 4.5) at 30° C. β-glucosidase (50 mg from almonds, Sigma) was added and the mixture was stirred for a week. The solution was evaporated in vacuo and purified by chromatography to give the product as a crystalline solid (8.2 g, 55%).

EXAMPLE 26

Preparation of isopropyl 6-O-octanoyl-α-D-glucopyranoside

To a stirred solution of isopropyl α-D-glucopyranoside (1.1 g, 5 mmol) and octanoic acid (0.9 g, 6.25 mmol) in 100 ml 2-butanone was added immobilized lipase (0.5 g Lipozyme TM, see example 8). Stirring was continued at 60° C. for 48 hours. The enzyme was removed by filtration and the solvent was removed in vacuo followed by chromatography yielding 1.2 g (70%) of the product $^1$H NMR (400 MHz, $CDCl_3$) δ: 0.88 (t, J=6.7 Hz, 3H); 1.19 (d, J=6.1 Hz, 3H); 1.24 (d, J=6.2 Hz, 3H); 1.28 (m, 8H); 1.62 (m, 2H); 2.34 (m, 2H); 3.35 (t, J=9.4 Hz, 1H); 3.50 (dd, J=4.0 and 9.5 Hz, 1H); 3.73 (t,J=9.3 Hz, 1H); 3.85 (m, 1H); 3.92 (m, 1H) 4.35 (m, 2H); 4.96 (d, J=3.9 Hz, 1H).

EXAMPLE 27

Preparation of n-butyl 6-O-octanoyl-β-D-glucopyranoside

The title compound was prepared according to the method described in example 26 using n-butyl β-D-glucopyranoside (1.0 g, 4.2 mmol) in 2-butanone (50 ml) in a 25% yield after 24 hours: $^1$H NMR (400MHZ, $CDCl_3$) δ: 0.90 (m, 6H); 1.29 (M, 8H); 1.37 (m, 2H); 1.61 (m, 4H); 2.35 (m, 2H); 3.35 (m, 2H); 3.50 (m, 3H); 3.85 (m, 1H); 4.27 (d, J=8 HZ, 1H); 4.28 (m, 1H); 4.38 (m, 1H).

EXAMPLE 28

Preparation of ethyl 6-O-octanoyl-α-D-glucopyranoside

After a reaction time of 48 hours the title compound was prepared in a 70% yield according to example 26 using an immobilized lipase from a *Pseudomonas cepacia* (0.5 g, prepared as described in Danish Patent application No. 3993/87) and ethyl-α-D-glucopyranoside (1.04 g, 5 mmol, prepared as described in example 25). For $^1$H NMR see table 4 b.

EXAMPLE 29

Preparation of ethyl 6-O-dodecanoyl-D-glucopyranoside

The title compound was prepared according to example 1 using 1/10 of the molar amounts and an immobilized lipase prepared from a *Humicola lanuginosa* (3.0 g prepared as described in Danish Patent application No. 3183.000/DK) as a Catalyst yielding a crude product (100 g containing 83% monoester and 15% diester and 2% ethyl D-glucopyranoside) after a reaction time of 16 hours.

In tables 4 a and 4 b $^1$H-NMR and $^{13}$C-NMR data for ethyl 6-O-acylucopyranosides of formula I are given.

TABLE 4a

| | Ethyl 6-O-acyl-β-D-glucopyranosides | | | | | |
|---|---|---|---|---|---|---|
| | $C_8$ | $C_{10}$ | $C_{12}$ | $C_{14}$ | $C_{16}$ | $C_{18}$ |
| C1 | 102.3 | 102.4 | 102.3 | 102.4 | 102.3 | 102.4 |
| C2 | 73.3 | 73.4 | 73.4 | 73.4 | 73.3 | 73.5 |
| C3 | 76.0 | 76.3 | 76.2 | 75.9 | 76.0 | 75.8 |
| C4 | 70.1 | 70.4 | 70.4 | 70.1 | 70.1 | 70.0 |
| C5 | 73.8 | 73.9 | 73.8 | 73.9 | 73.8 | 74.0 |
| C6 | 63.3 | 63.5 | 63.5 | 63.2 | 63.3 | 63.0 |
| $CH_3CH_2O—$ | 65.5 | 65.4 | 65.4 | 65.5 | 65.5 | 65.6 |
| $CH_3CH_2O—$ | 15.0 | 15.0 | 15.0 | 15.0 | 15.0 | 15.0 |
| COO | 174.3 | 174.1 | 174.1 | 174.5 | 174.4 | 174.3 |
| H1 | 4.28 | 4.28 | 4.28 | 4.29 | 4.28 | 4.28 |
| H2 | 3.37 | 3.37 | 3.37 | 3.37 | 3.36 | 3.37 |
| H3 | 3.55 | 3.54 | 3.54 | 3.54 | 3.54 | 3.57 |
| H4 | 3.37 | 3.37 | 3.37 | 3.37 | 3.36 | 3.37 |
| H5 | 3.47 | 3.47 | 3.48 | 3.48 | 3.46 | 3.46 |
| H6a | 4.35 | 4.35 | 4.32 | 4.31 | 4.35 | 4.30 |
| H6b | 4.35 | 4.35 | 4.37 | 4.38 | 4.35 | 4.47 |
| $CH_3CH_2O—$ | | | | | | |
| a | 3.61 | 3.61 | 3.62 | 3.61 | 3.61 | 3.61 |
| b | 3.94 | 3.94 | 3.94 | 3.94 | 3.94 | 3.96 |

TABLE 4b

| | Ethyl 6-O-acyl-α-D-glucopyranosides | | | | | |
|---|---|---|---|---|---|---|
| | $C_8$ | $C_{10}$ | $C_{12}$ | $C_{14}$ | $C_{16}$ | $C_{18}$ |
| C1 | 98.3 | 98.3 | 98.3 | 98.0 | 98.1 | 98.3 |
| C2 | 72.1 | 72.2 | 72.2 | 72.0 | 71.9 | 72.1 |
| C3 | 74.4 | 74.5 | 74.5 | 74.3 | 74.1 | 74.4 |
| C4 | 70.6 | 70.7 | 70.6 | 70.0 | 70.1 | 70.6 |
| C5 | 69.9 | 70.0 | 70.0 | 69.8 | 69.7 | 70.0 |
| C6 | 63.7 | 63.7 | 63.6 | 63.1 | 63.2 | 63.6 |
| $CH_3CH_2O—$ | 63.9 | 63.9 | 63.9 | 93.8 | 63.7 | 63.9 |
| $CH_3CH_2O—$ | 15.0 | 15.0 | 15.0 | 14.9 | 14.9 | 15.0 |
| COO | 174.2 | 174.2 | 174.2 | 174.4 | 174.3 | 174.2 |
| H1 | 4.87 | 4.87 | 4.88 | 4.88 | 4.87 | 4.87 |
| H2 | 3.51 | 3.51 | 3.51 | 3.52 | 3.51 | 3.51 |
| H3 | 3.76 | 3.75 | 3.75 | 3.75 | 3.75 | 3.75 |
| H4 | 3.35 | 3.35 | 3.34 | 3.34 | 3.34 | 3.34 |
| H5 | 3.78 | 3.78 | 3.77 | 3.77 | 3.78 | 3.77 |
| H6a | 4.32 | 4.32 | 4.28 | 4.31 | 4.31 | 4.29 |
| H6b | 4.37 | 4.36 | 4.45 | 4.31 | 4.37 | 4.41 |
| $CH_3CH_2O—$ | | | | | | |
| a | 3.57 | 3.57 | 3.56 | 3.56 | 3.56 | 3.5 |

TABLE 4b-continued

| | Ethyl 6-O-acyl-α-D-glucopyranosides | | | | | |
|---|---|---|---|---|---|---|
| | $C_8$ | $C_{10}$ | $C_{12}$ | $C_{14}$ | $C_{16}$ | $C_{18}$ |
| b | 3.77 | 3.77 | 3.78 | 3.77 | 3.77 | 3.77 |

The columns in tables 4 a and 4 b give the data for compounds wherein the parent fatty acid (RCOOH) contains 8, 10, 12, 14, 16 and 18 carbon atoms corresponding to the column titles $C_8$, $C_{10}$, $C_{12}$, $C_{14}$, $C_{16}$ and $C_{18}$, respectively. $C_1$–$C_6$ indicate carbons in the glucoside and H1–H6b indicate hydrogen atoms in the glucoside for which $^{13}C$ NMR and $^1H$ NMR, respectively, are given in these tables.

EXAMPLE 30

Preparation of ethyl 6-O-octanoyl-D-galactoside

The title compound was prepared according to example 12 using ethyl D-galactoside (11.5 g, 56 mmol, prepared according to example 31), octanoic acid (16 g, 111 mmol) and Lipozyme (2 g, see example 8). After 24 hours the product was recovered in a yield of 80%.

EXAMPLE 31

Preparation of ethyl D-galactoside

The title compound was prepared according to example 10 using galactose. The product (being a mixture of ethyl D-galactopyranoside and ethyl D-galactofuranoside) was isolated in quantitative yield.

EXAMPLE 32

Preparation of 2,3-isopropylidene-glyceryl 6-O-hexadecanoyl-α-D-galactopyranoside The title compound was prepared as described in example 26 in a yield of 70% after a reaction time of 16 hours.

EXAMPLE 33

Preparation ethyl 6-O-octanoyl-α-D-glucopyranoside by transesterification

The title compound was prepared according to example 26 using ethyl-α-D-glucopyranoside (1.04 g, 5 mmol) and methyl octanoate (1.8 g, 11 mmol) as substrates. After a reaction time of 24 hours the product was isolated in a yield of 10%.

EXAMPLE 34

Experiments were performed in a Terc-O-tometer using the following conditions:

| | |
|---|---|
| Washing time: | 20 min. |
| Temperature: | 25° C. |
| Water: | 9°dH |
| Test material: | EMPA 112 (7 · 7 cm) |
| Detergent: Sodium triphosphate | 1.75 g/l |
| Sodium metasilicate | 0.40 g/l |
| CMC | 0.05 g/l |
| EDTA | 0.01 g/l |
| Sodium sulphate | 2.00 g/l |
| Tensid | 0.60 g/l |

The tensid used was 75% of a linear alkyl benzene sulphonate (LAS, Nansa S80) and 25% of a compound of formula I. The results obtained appear from table 5 below:

TABLE 5

| Test compound | % residual fat weight/weight |
|---|---|
| Berol 065 | 2.44 |
| Berol 160 | 2.55 |
| Ethyl 6-O-octanoylglucoside | 2.38 |
| Ethyl 6-O-decanoylglucoside | 2.24 |
| Ethyl 6-O-dodecanoylglucoside | 2.30 |
| Ethyl 6-O-hexadecanoylglucoside | 2.31 |

We claim:

1. A compound of the formula $$R-COO-X-OR^1$$

wherein
X represents a monosaccharide containing one hexose or pentose unit which carries (a) the group $OR^1$ at the anomeric carbon atom and (b) the group RCOO— at a primary hydroxy group;
$R^1$ represents alkyl with 2–6 carbon atoms or one of the following groups $$-CH_2-CH(O-C(CH_3)_2-O)-CH_2 \quad -CH_2-CH(-O-)Y$$

$$-CH_2-CH(O-C(=O)-O)-CH_2$$

wherein
Y represents methylene or ethylene; and
R represents alkyl with 4–24 carbon atoms.

2. The compound according to claim 1, wherein $R^1$ is alkyl with 2–6 carbon atoms.

3. The compound according to claim 2, wherein $R^1$ is ethyl, propyl, isopropyl or butyl.

4. The compound according to claim 3, wherein $R^1$ is ethyl or isopropyl.

5. The compound according to claim 1, wherein X is glucose, fructose, ribose, mannose or galactose.

6. The compound according to claim 2, wherein X is glucose.

7. The compound according to claim 5, wherein X is galactose.

8. The compound according to claim 1, wherein the moiety R—COO— contains 6–22 carbon atoms.

9. The compound according to claim 8, wherein RCOO is hexanoyloxy, heptanoyloxy, octanoyloxy, nonanoyloxy, decanoyloxy, dodecanoyloxy, tetradecanoyloxy, hexadecanoyloxy, octadecanoyloxy, eicosanoyloxy, docosanoyloxy, cis-9-octadecenoyloxy, cis,cis-9,12-octadecadienoyloxy or cis,cis,cis-9,12,15-octadecatrienoyloxy.

10. The compound according to claim 1 being ethyl 6-O-hexanoylglucoside,, ethyl 6-O-heptanoylglucoside, ethyl 6-O-octanoylglucoside, ethyl 6-O-nonanoylglucoside, ethyl 6-O-decanoylglucoside, ethyl 6-O-dodecanoylglucoside, ethyl 6-O-tetradecanoylglucoside, ethyl 6-O-hexadecanoylglucosdie, ethyl 6-O-octadecanoylglucoside, ethyl 6-O-eicosanoylglucoside, ethyl 6-O-docosanoylglucoside, ethyl 6-O-cis-9- octadecenoylglucoside, ethyl 6-O-cis,cis-9,12-octadecadienoylglucoside, ethyl 6-O-cis,cis,cis,-9,12,15-octadecatrienoylglucoside, isopropyl 6-O-octanoyl-glucoside, isopropyl 6-O-nonanoylglucoside, isopropyl 6-O-decanoylglucoside, isopropyl 6-O-dodecanoyl-glucoside, isopropyl 6-O-tetradecanoylglucoside, isopropyl 6-O-hexadecanoylglucoside, isopropyl 6-O-octadecanoylglucoside, isopropyl 6-O-eicosanoylglucoside, isopropyl 6-O-docosanoylglucoside, isopropyl 6-O-cis-9-octadecenoylglucoside, isopropyl 6-O-cis,cis-9,12-octadecadienoyl-glucoside, isopropyl 6-O-cis,cis,-cis-9,12,15-octadecatrienoyl-glucoside, propyl 6-O-hexanoylglucoside, propyl 6-O-heptanoyl-glucoside, propyl 6-O-octanoylglucoside, propyl 6-O-nonanoyl-glucoside, propyl 6-O-decanoylglucoside, propyl 6-O-dodecanoyl-glucoside, propyl 6-O-tetradecanoylglucoside, propyl 6-O-hexa-decanoylglucoside, propyl 6-O-octadecanoylglucoside, propyl 6-O-eicosanoylglucoside, propyl 6-O-docosanoylglucoside, propyl 6-O-cis-9-octadecenoylglucoside, propyl 6-O-cis,cis-9,12-octadecadienoylglucoside, propyl 6-O-cis,cis,cis-9,12,15-octadecatrienoylglucoside, butyl 6-O-hexanoyl-glucoside, butyl 6-O-heptanoylglucoside, butyl 6-octanoylglucoside, butyl 6-O-nonanoylglucoside, butyl 6-O-decanoylglucoside, butyl 6-O-dodecanoylgluco-side, butyl 6-O-tetradecanoylglucoside, butyl 6-O-hexadecanoylglucoside, butyl 6-O-octadecanoylglucoside, butyl 6-O-eicosanoylglucoside, butyl 6-O-docosanoyl-glucoside, butyl 6-O-cis-9-octadecenoylglucoside, butyl 6-O-cis,cis-9,12-octadecadienoyl-glucoside or butyl 6-O-cis,cis,cis-9,12,15-octadecatrienoyl-glucoside.

11. A process for the production of a compound of the formula I $$R—COO—X—OR^1 \quad (I)$$

wherein
X represents a monosaccharide containing one hexose or pentose unit which carries (a) the group $OR^1$ at the anomeric carbon atom and (b) the group RCOO— at a primary hydroxy group;
$R^1$ represents alkyl with 2–6 carbon atoms or one of the following groups

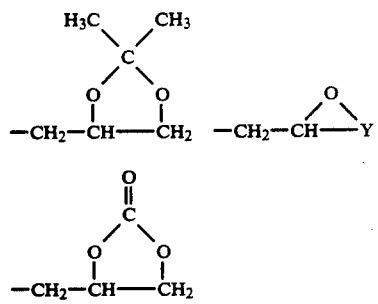

wherein
Y represents methylene or ethylene; and
R represents alkyl with 4–24 carbon atoms, which comprises reacting an acid or ester of formula II $$R—COOR^2 \quad (II)$$

wherein R is as defined above and $R^2$ is hydrogen or lower alkyl, with a glycoside of the formula III $$HO—X—OR^1 \quad (III)$$

wherein X and $R^1$ is as defined above and the group $OR^1$ is at the anomeric carbon atom, in the presence of a lipase as a catalyst in a reaction medium which is non-aqueous or contains only the approximate amount of water which is needed to ensure a good reactivity and lift-time of said lipase.

12. The process according to claim 11, wherein said lipase is a lipase obtained from a species of Mucor, Humicula, Pseudomonas or Candida.

13. The process according to claim 12, wherein said lipase is a lipase obtained from *Candida Antarctica*.

14. The process according to claim 1, wherein said lipase is a lipase obtained from *Mucor Miehei*.

15. The process according to claim 11, wherein said lipase catalyst is an immobilized lipase catalyst.

16. The process according to claim 11, wherein said reaction is carried out in an organic solvent other than said acid or ester of formula II.

17. The process according to claim 11, wherein the reaction is carried out in a solvent which is said acid or ester of formula II.

18. The process according to claim 11, wherein $R^1$ is alkyl of 2–6 carbon atoms.

19. The process according to claim 18, wherein $R^1$ is ethyl, propyl, isopropyl or butyl.

20. The process according to claim 19, wherein $R^1$ is ethyl or isopropyl.

21. The process according to claim 11, wherein X is glucose, fructose, ribose, mannose or galactose.

22. The process according to claim 21, wherein X is glucose.

23. The process according to claim 21, wherein X is galactose.

24. The process according to claim 11, wherein the moiety R—COO— contains 6–22 carbon atoms.

25. The process according to claim 24, wherein RCOO is hexanoyloxy, heptanoyloxy, octanoyloxy, nonanoyloxy, decanoyloxy, dodecanoyloxy, tetradecanoyloxy, hexadecanoyloxy, octadecanoylocy, eicosanoyloxy, docosanoyloxy, cis-9-octadecenoyloxy, cis,cis-9,12-octadecadienoyloxy or cis,cis,cis-9,12,15-octadecatrienoyloxy.

26. A process for the production of a 6-$C_4$ to $C_{24}$ acyl-1-$C_2$ to $C_6$ alkyl glucoside, which comprises reacting an acid or ester of formula II $$R—COOR^2 \quad (II)$$

wherein R is alkyl of 4–24 carbon atoms and $R^2$ is hydrogen or lower alkyl, with a 1-$C_2$ to $C_6$ alkylglucoside in the presence of an immobilized lipase as a catalyst in a reaction medium which is non-aqueous or contains only the approximate amount of water which is needed to ensure a good reactivity and lift-time of said lipase.

27. The process according to claim 26, wherein said lipase is a lipase obtained from a species of Mucor, Humicula, Pseudomonas or Candida.

28. The process according to claim 27, wherein said lipase is a lipase obtained from *Candida Antarctica*.

29. The process according to claim 27, wherein said lipase is a lipase obtained from *Mucor Miehei*.

30. The process according to claim 26, wherein said reaction is carried out in an organic solvent other than said acid or ester of formula II.

31. The process according to claim 26, wherein said reaction is carried out in a solvent which is said acid or ester of formula II.

32. The process according to claim 26, wherein $R^1$ is alkyl with 2–4 carbon atoms.

33. The process according to claim 32, wherein $R^1$ is ethyl, propyl, isopropyl or butyl.

34. The process according to claim 33, wherein $R^1$ is ethyl.

35. The process according to claim 26, wherein the moiety R—COO— contains 6–22 carbon atoms.

36. The process according to claim 35, wherein RCOO is hexanoyloxy, heptanoyloxy, octanoyloxy, nonanoyloxy, decanoyloxy, dodecanoyloxy, tetradecanoyloxy, hexadecanoyloxy, octadecanoylocy, eicosanoyloxy, docosanoyloxy, cis-9-octadecenoyloxy, cis,cis-9,12-octadecadienoyloxy or cis,cis,-9,12,15-octadecatrienoyloxy.

37. In a cleaning composition comprising a surfactant, the improvement wherein said surfactant comprises a compound according to claim 1.

38. In a cleaning composition comprising a surfactant, the improvement wherein said surfactant comprises a compound according to claim 6.

* * * * *